US008057805B1

(12) United States Patent
Kuo et al.

(10) Patent No.: US 8,057,805 B1
(45) Date of Patent: Nov. 15, 2011

(54) *EDWARDSIELLA ICTALURI* E-ICT-VL33 STRAIN, VACCINES THEREOF, AND A METHOD FOR PROTECTING FISHES USING SAID VACCINES

(75) Inventors: Tsun-Yung Kuo, I-Lan (TW); Hsu Chung Gabriel Chen, Taipei (TW)

(73) Assignee: Schweitzer Biotech Company Ltd., Taipei (TW)

( * ) Notice: Subject to any disclaimer, the term of this patent is extended or adjusted under 35 U.S.C. 154(b) by 0 days.

(21) Appl. No.: 12/845,965

(22) Filed: Jul. 29, 2010

(51) Int. Cl.
*A61K 39/02* (2006.01)
*A61K 39/108* (2006.01)
*C12N 1/20* (2006.01)

(52) U.S. Cl. ............... 424/234.1; 424/184.1; 424/241.1; 435/252.1

(58) Field of Classification Search ........................ None
See application file for complete search history.

(56) References Cited

OTHER PUBLICATIONS

Thinh et al., "Combined immersion and oral vaccination of Vietnamese catfish (*Pangasianodon hypophthalmus*) confers protection against mortality caused by *Edwardsiella ictaluri*,"Fish & Shellfish Immunology, 27 (2009) 773-776.

*Primary Examiner* — Padma Baskar
(74) *Attorney, Agent, or Firm* — Muncy, Geissler, Olds & Lowe, PLLC

(57) ABSTRACT

A novel *Edwardsiella ictaluri* E-ict-VL33 strain, a vaccine derived from the novel *Edwardsiella ictaluri* E-ict-VL33 strain, especially in immersion form and oral form, and a method for protecting fishes from the infection of *Edwardsiella ictaluri*, especially catfish, the method including a primary immersion immunization using immersion vaccine, and after an appropriate period, boosting by oral vaccination, resulting in a strong and long-lasting immunity for fishes.

12 Claims, 3 Drawing Sheets

SEQUENCE LISTING

<160> NUMBER OF SEQ ID NOS: 2

<210> SEQ ID NO 1
<211> LENGTH: 1410
<212> TYPE: DNA
<213> ORGANISM: Edwardsiella ictaluri E-ict-VL33
<220> FEATURE:
<223> OTHER INFORMATION: 16S rDNA of Edwardsiella ictaluri E-ict-VL33

<400> SEQUENCE: 1

```
gcggacgggt gagtaatgtc tggggatctg cctgatggag gggataact actggaaacg     60

gtagctaata ccgcataacg tcgcaagacc aaagtggggg accttcgggc ctcatgccat    120

cagatgaacc cagatgggat tagctagtag gtggggtaat ggctcaccta ggcgacgatc    180

cctagctggt ctgagaggat gaccagccac actggaactg agacacggtc cagactccta    240

cgggaggcag cagtggggaa tattgcacaa tgggcgcaag cctgatgcag ccatgccgcg    300

tgtatgaaga aggccttcgg gttgtaaagt actttcagta gggaggaagg tgtgagcgtt    360

aatagcgttc acaattgacg ttacctacag aagaagcacc ggctaactcc gtgccagcag    420

ccgcggtaat acggagggtg caagcgttaa tcggaattac tgggcgtaaa gcgcacgcag    480

gcggtttgtt aagttggatg tgaaatcccc gggcttaacc tgggaactgc atccaagact    540

ggcaagctag agtctcgtag agggaggtag aattccaggt gtagcggtga aatgcgtaga    600

gatctggagg aataccggtg gcgaaggcgg cctcctggac gaagactgac gctcaggtgc    660

gaaagcgtgg ggagcaaaca ggattagata ccctggtagt ccacgctgta aacgatgtcg    720

atttggaggt tgtgcccttg aggcgtggct tccgaagcta acgcgttaaa tcgaccgcct    780

ggggagtacg gccgcaaggt taaaactcaa atgaattgac gggggcccgc acaagcggtg    840

gagcatgtgg tttaattcga tgcaacgcga agaaccttac ctactcttga catccagcga    900

atcctgtaga gatacgggag tgccttcggg aacgctgaga caggtgctgc atggctgtcg    960

tcagctcgtg ttgtgaaatg ttgggttaag tcccgcaacg agcgcaaccc ttatcctttg   1020

ttgccagcgg ttaggccggg aactcaaagg agactgccag tgataaactg gaggaaggtg   1080

gggatgacgt caagtcatca tggcccttac gagtagggct acacacgtgc tacaatggcg   1140

tatacaaaga gaagcgacct cgcgagagca agcggacctc ataaagtacg tcgtagtccg   1200

gattggagtc tgcaactcga ctccatgaag tcggaatcgc tagtaatcgt ggatcagaat   1260

gccacggtga atacgttccc gggccttgta cacaccgccc gtcacaccat gggagtgggt   1320

tgcaaaagaa gtaggtagct taaccttcgg gagggcgctt accactttgt gattcatgac   1380

tggggtgaag tcgtaacaag tacgtggact                                    1410
```

<210> SEQ ID NO 2
<211> LENGTH: 1876
<212> TYPE: DNA
<213> ORGANISM: Edwardsiella ictaluri E-ict-VL33
<220> FEATURE:
<223> OTHER INFORMATION: partial sequence of the plasmid pEI1 of
      Edwardsiella ictaluri E-ict-VL33

<400> SEQUENCE: 1

```
atgccattgc atgtcggcac cgggcatatc cccgccacca tcagtaataa ccgcattcat     60

cgcatcgcca gcgctaatac cccaccggag atgagcgtgc gggagaatat tcaggagttt    120

ttctgctcaa cacataagtc agaggccctt aactgccttt gggaaatttg tcatcctcca    180

gtcggaacta cacgggacgc tgtagcgggt agatttgagc agctcaagag actcgcctat    240
```

-continued

```
ccgggatacg agaataatat ccagtctggc cgaaatggag ataacagctt ctgtattttg    300

gatgaagacg gacaggaaat gttatctgta atccttggtg atgccgatac gtataccgtt    360

atctatccgg gtggcgagat gacacatgac ctcagccttt ccgcaccaca aggagatgag    420

ggtctcctga tattaggtgc ttccgacacc gtgggaccac aaacagaggg agagtataaa    480

gctgcctggt cagcgtggga aagggctgcg ccaccagaag aggcagaaga ccgagccaag    540

acagtacggg agctgcgtca ctgcctgcga tataacaccc ggctggatgt ctctaacacc    600

aaactaacca gtttgccgcc tctgccgacc ggactgaaga ggctggatgt ctctggtact    660

ggactgacca gcctgccgcc actccatcca aactgcagag gctggatatc tctaacactc    720

ctatgccaag gctaccgtca ctgccctcca gactgcagag actggatgtc tctaacaccc    780

acctggccaa ccttccggaa atcatcgcca atttatcgca gaggacaacg gtaagactgc    840

agagtaactc cctgtcagaa cgtacacttc agatgatcaa taaacccggc tatcagggac    900

ccaggatagt tgatatggca acatcttcta atcatcagga aaccagagcc ctgcacttgg    960

cggtggcgga ctggctgacg ccggcggaag cggacgagga ggcttccgct aaaagatggt   1020

gggctatcgg gaaggaagac gatgccgccg ccttcagcac tttcctcgac cggctgaaaa   1080

agacgaaaaa taatcaggca accgattttc acgtgcagat agccagctgg attagccagc   1140

tggcgcagga tgatgagcta agagccaaaa cctttgacat ggcgacagag tcaacctcaa   1200

gctgtgagga cagggtcacg ctggcaatga gcaatatgta gagtgtgcaa ctggtccata   1260

atgctgaaaa agggaaattc gaccgtgata tcccggggct cgtgtcagcg gggcgtgaaa   1320

tgttccgcct agaacaacta gatctaattg cccgtgagaa ggtaaaaaag ctacgctttt   1380

tcgatgaaat tgagataaaa aaatggctat cagaacaaac tgaaagaatc acttgaacta   1440

acctccaaac ccgtcggccg gcgcattgag cagattccgc ggtcaaggcc atcgacgttg   1500

ggtcatctgg ggggaaccga gcgcgggact gggagcatcc tctagcgttt gaggtggccc   1560

cagagggcgc ccgtcctcgc gtatcaggga tatagagtct cgcgtcacaa ttgacttcat   1620

agatggagga gcagtcggtg gcgttctcca gcagcgggga atcccccaac agctgggtca   1680

gcagcagata tagggggttt ctctgcagat ggaaacgaca cctcagtatc ctccatttat   1740

ggaaatcatt tccccaccag aacctatatc cgctatagtc aggaacgcgg gatctccggg   1800

gccatctcaa agttgagaaa acccgagtcc cctccgtttt ctccgagcgc acaacagacc   1860

accccggctc gaaaaa                                                   1876
```

*EDWARDSIELLA ICTALURI* E-ICT-VL33 STRAIN, VACCINES THEREOF, AND A METHOD FOR PROTECTING FISHES USING SAID VACCINES

BACKGROUND OF THE INVENTION

1. Field of the Invention

The invention relates to a novel *Edwardsiella ictaluri* E-ict-VL33 strain, vaccines derived therefrom, and a method for protecting fishes using said vaccines.

2. Brief Description of the Prior Art

*Edwardsiella* is a type of small Gram-negative rod bacterium. The host of *Edwardsiella* includes Catfish, Eel, Tilapia and other warm water fishes. *Edwardsiella ictaluri* is one member of *Edwardsiella. E. ictaluri* that can infect catfish, thereby causing *Edwardsiella* septicemia. Acute *Edwardsiella* septicemia usually results in typical bacterial septicemia with a high mortality rate for fishes. Chronic *Edwardsiella* septicemia can result in Hole-in-the-head syndrome, septicemia or, ultimately, death.

*Edwardsiella* septicemia occurs worldwide and causes high mortality and considerable economic damage to the catfish industry, especially in Vietnam and the USA. Microbiological infections with *E. ictaluri* play a major role in catfish (*Pangasianodon hypophthalmus*) farming in Vietnam [Dung T T, et al., Microbe Drug Res 2008.] and were first observed in the Mekong River Delta in 1999 [Ferguson H W, et al. J Fish Dis 2001; 24:509-13]. *E. ictaluri* infections are seen in the USA in channel catfish (*Ictalurus punctatus*) and also in walking catfish in Thailand [Kasornchandra J, et al. J Fish Dis 1987; 10:137-8]. All catfish species are susceptible to *E. ictaluri* and the disease causes major damage in Basa Tra fish in the Mekong delta and other places where the fish is cultured in Vietnam. Many ways of protecting the fish have been tried but none so far have been very successful.

The use of antibiotics to counteract bacterial infections has been successful in some instances but not in others, especially because of widespread resistance as a result of extensive and non-controlled use of many different antibiotics either alone or in various combinations. The situation is worsened by the fact that *E. ictaluri*, and thus resistant *E. ictaluri*, can survive in the mud of a pond for up to 3 months. Furthermore, the use of antibiotics and chemotherapeutics is discouraged because of both environmental and residual problems, and long-term use of antibiotics is not a sustainable control method for fish diseases. However, preventing and protecting the fish from *Edwardsiella* septicemia cannot be achieved by using antibiotics which can only control the spreading of *Edwardsiella* septicemia.

Vaccination as a preventive measure to control infections with *E. ictaluri* has been tried in various catfish species. Until now, not a single vaccination or combination of vaccinations has been proven as particularly successful in the field. It has been claimed that an attenuated vaccine is able to help in the control of the disease but, to date, the product has not made major inroads in the field. Besides that, oral delivery of vaccine antigens to fish is the preferred method for several reasons. However the limitations of this method include lack of immune efficacy [Gudding R, et al. Vet Immunol Immunopathol 1999].

In view of the above-described disadvantages associated with conventional techniques, the inventor had developed a novel *Edwardsiella ictaluri* E-ict-VL33 strain, vaccines thereof, and a method for protecting fishes using said vaccines.

SUMMARY OF THE INVENTION

The meaning of the technical and scientific terms as described herein can be clearly understood by the person skilled in the art.

One object of the invention is to provide a novel *Edwardsiella ictaluri* E-ict-VL33 strain, which had been identified as a novel strain of *E. ictaluri.*

Another object of the invention is to provide a vaccine, which is prepared from the inactivated *E. ictaluri* E-ict-VL33 strain. Said vaccine can be prepared as an immersion form, oral form or other suitable form.

Still another object of the invention is to provide a method for improving the immunity of fish against *E. ictaluri*, and further preventing and protecting fishes from infection of *E. ictaluri* by using said vaccines.

In order to achieve the above-described objects of the invention, the invention comprises various aspects as will be discussed below.

In one aspect of the invention, a novel *E. ictaluri* E-ict-VL33 strain is to be provided. This strain was isolated from infected tra catfish (*Pangasius hypophthalmus*). The isolated E-ict-VL33 strain had been cultured and identified as a novel *E. ictaluri* strain, and was named as *E. ictaluri* E-ict-VL33 strain, and had been deposited in the biological resource center ATCC Patent Depository, located at 10801 University Blvd., Manassas, Va. 20110, on Mar. 8, 2010, with an ATCC deposit number PTA-10711 and identification reference by deposit: *Edwardsiella ictaluri*: E-ict-VL33. The bacterium strain of the invention has been used herein is an example, but the invention will not be limited thereto, all kind of suitable strain are comprised in the invention.

In another aspect, the invention provides a vaccine composition comprising said novel *E. ictaluri* strain. In a preferred embodiment, said vaccine composition is a vaccine. The vaccine comprises an effective amount of inactivated *E. ictaluri* E-ict-VL33 strain and a pharmaceutically acceptable vehicle. It can be prepared in any dosage form suitable for the invention. Said suitable form of the invention includes, but is not limited to, oral-form, immersion-form, injection-form or other suitable forms for the invention.

An immersion vaccine is obtained by using an inactivating agent to inactivate or kill the *E. ictaluri* E-ict-VL33 strain (i.e., an inactivation process). The inactivated bacteria is then suspended in a buffer solution. This process allows an immersion vaccine to be obtained.

An oral vaccine is obtained by using an inactivating agent to inactivate or kill the *Edwardsiella ictaluri* E-ict-VL33 strain (i.e., an inactivation process). The inactivated bacteria is then suspended in a buffer solution to form a bacterial suspension, and the bacterial suspension is mixed with an adjuvant to form a mixture. The mixture is then homogenously emulsified by a homogenizer with high shear force. This process allows the oral vaccine to be obtained. Said oral vaccine can further be spray coated on the outside of a feed to deliver the oral vaccine to fish. Also, the coated feed can further be sprayed with edible oil, such as plant oil and/or animal oil (in particular, a fish oil), to improve the delivery efficiency of the oral vaccine.

The term "inactivation" as described herein includes, but is not limited to, treatment with inactivation agent, heat treatment, and other general methods to inactivate or kill the bacteria. The inactivation agent includes, but is not limited to, formaldehyde, binary ethyleneimine (BEI) or other suitable inactivation agents.

The pharmaceutically acceptable vehicle includes, but is not limited to, solvent, emulsifier, suspending agent, decomposer, binding agent, excipient, stabilizing agent, chelating agent, diluent, gelling agent, preservative, lubricant, surfactant, adjuvant or other suitable vehicle.

The adjuvant includes, but is not limited to, oleaginous adjuvant (such as mineral oil, plant oil, animal oil, Freund's Complete Adjuvant, Freund's Incomplete Adjuvant, etc.), aqueous adjuvant (such as aluminum hydroxide), two-phase oleaginous adjuvant (such as water/oil/water form (w/o/w)) etc, and biological (such as adjuvant oligonucleotide and toxoid). The two-phase oleaginous adjuvant comprises a surfactant and an oleaginous substance. The surfactant is selected from the group consisting of: at least one of sorbitol fatty acid ester, the concentrate of sorbitol fatty acid ester and ethylene oxide (or propylene oxide), mannitol fatty acid ester, the concentrate of mannitol fatty acid ester and ethylene oxide (or propylene oxide), modified mannitol fatty acid ester with a hydrophilic group which is selected from the group consisting of: at least one of carboxylic acid, amine, amide, alcohol, polyol, ether and oxide; anhydromannitol fatty acid ester, modified anhydromannitol fatty acid ester with a hydrophilic group which is selected from the group consisting of: at least one of carboxylic acid, amine, amide, alcohol, polyol, ether and oxide; saccharose fatty acid ester, the concentrate of saccharose fatty acid ester and ethylene oxide (or propylene oxide), glycerol fatty acid ester, the concentrate of glycerol fatty acid ester and ethylene oxide (or propylene oxide), the concentrate of fatty acid and ethylene oxide (or propylene oxide), the concentrate of fatty alcohol and ethylene oxide (or propylene oxide), and glycerophospholipid. The oleaginous substance is selected from the group consisting of: at least one of mineral oil, plant oil and animal oil. In a preferred embodiment, said oleaginous substance is animal oil, especially fish oil.

In addition, the invention also provides a composition comprising the novel *E. ictaluri* strain. The composition can be applied to various suitable products such as challenge composition containing live bacteria, vaccine containing inactivated bacteria etc.

In third aspect, the invention provides a method for improving the immunity of fishes against *E. ictaluri*, further preventing and protecting fishes from infection of *E. ictaluri* by using said vaccines. According to the following examples, a method comprising a primary immunization by immersion vaccination at first and, after an appropriate time period, a subsequent oral vaccination boosting, can give a protecting effect higher than would be obtained by other vaccination routes. Here, fishes refer to those that are susceptible to *Edwardsiella ictaluri* infection, in particular, catfishes. The invention also provides the use of *Edwardsiella ictaluri* E-ict-VL33 in preparation of a vaccine to protect fish from infection of *Edwardsiella ictaluri.*

The term "effective amount" refers to the amount of inactivated bacteria used to improve the immunity of fish against *E. ictaluri*, and then the amount of inactivated bacteria used to prevent and protect the fish from the infection of *E. ictaluri* or disease derived thereto in further inoculation.

The term "prevent and protect" is intended to mean that, compared to the immunity of untreated fish, the immunity of treated fish against *E. ictaluri* is improved and the survival rate of treated fish after infection of *E. ictaluri* is higher than survival rate of untreated fish. Further inoculation of the amount of inactivated bacteria prevents and protects the fish from the infection of *E. ictaluri* or disease derived thereto.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENT

The invention will be illustrated by way of the following examples, but the invention will not be limited thereto.

EXAMPLE 1

Isolation and Identification of *Edwardsiella ictaluri* E-ict-VL33 Strain

An isolated E-ict-VL33 strain was isolated from infected tra catfish (*P. hypophthalmus*). Bacterial culture grown in Brain Heart Infusion (BHI, the composition of BHI are shown in Table 1) broth for 18 hours at 25-30° C. was used for experimental infection. Bacteria growth on BHI agar for 48 h at 30° C. was used for bacterial identification.

TABLE 1

The composition of BHI broth (Difco Laboratories, Sparks, MD)

| Composition | Content |
|---|---|
| Calf Brains, Infusion from 200 g | 7.7 g |
| Beef Heart, Infusion from 250 g | 9.8 g |
| Proteose Peptone | 10.0 g |
| Dextrose | 2.0 g |
| Sodium Chloride | 5.0 g |
| Disodium Phosphate | 2.5 g |
| Add water up to 1 liter | |
| Total | 1 liter |

The Characteristics of *Edwardsiella ictaluri* E-ict-VL33 Strain

Figure 1:
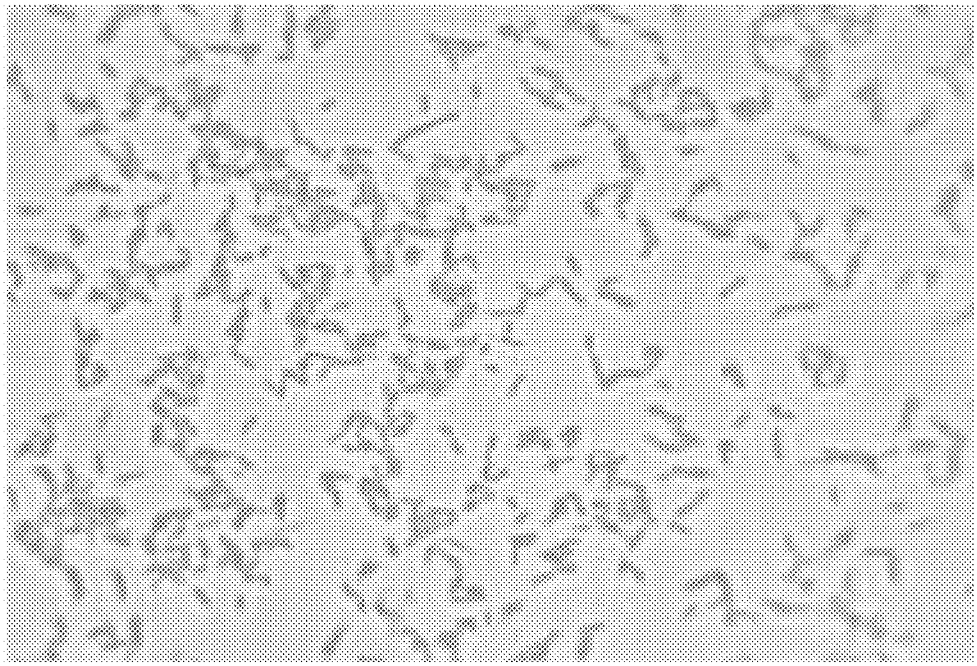
FIG. 1 shows the morphology of the novel *Edwardsiella ictaluri* E-ict-VL33 strain under microscope.

FIG. 1 shows that the isolated E-ict-VL33 strain is a rod bacterium. An analysis of Gram staining shows that the isolated E-ict-VL33 strain is a Gram-negative rod bacterium. Referring to Tables 2 to 4, these tables show the growth situation of the isolated E-ict-VL33 strain under different culture conditions such as different temperature, salinity or pH value. "+" represents that the growth of bacteria is slower and contains a lower concentration of bacteria. "++" represents that the bacteria have grown with less precipitation. "+++" represents that the bacteria have grown with higher precipitation. "−" represents that there no growth of bacteria can be observed. In addition, the isolated E-ict-VL33 strain can be cultured in a tryptic soy broth (TSB) or a brain heart infusion (BHI). Furthermore, Table 5 shows the carbohydrate metabolism performance of the isolated E-ict-VL33 strain. "+" represents that the carbohydrate can be metabolized by the isolated E-ict-VL33 strain.

TABLE 2

Culturing the isolated E-ict-VL33 strain at 28° C., under different pH values.

| | pH value | | | | | | |
|---|---|---|---|---|---|---|---|
| | 4 | 5 | 6 | 7 | 8 | 9 | 10 |
| 24 hr | − | + | + | ++ | + | + | + |
| 48 hr | − | ++ | +++ | +++ | +++ | ++ | ++ |

TABLE 3

Culturing the isolated E-ict-VL33 strain under different temperatures.

| Temperature | 37° C. | 37° C. (AC) | 20° C. (AC) | 20° C. | 28° C. |
|---|---|---|---|---|---|
| 24 hr | − | + | + | − | ++ |
| 48 hr | − | +++ | ++ | − | +++ |

Note:
"AC" stands for acclimatization. In a group labeled "AC," the bacteria is cultured for about 2 day at 28° C., then cultured in a ratio of 1:100 at another temperature. The other groups (i.e., those not labeled "AC") are colonies of bacteria incubated at different temperatures directly.

TABLE 4

Culturing the isolated E-ict-VL33 strain at 28° C., under different salinity.

| Salinity | 0.5% | 1% | 1.5% | 2% |
|---|---|---|---|---|
| 24 hr | + | + | + | − |
| 48 hr | ++ | ++ | ++ | − |

TABLE 5

The carbohydrate metabolism performance of the isolated E-ict-VL33 strain.

| Carbohydrate | Performance |
|---|---|
| D-Fructose | + |
| Inosine | + |
| D-Psicose | + |
| Uridine | + |
| D-Galactose | + |
| α-D-Glucose | + |
| D, L-Lactic acid | + |
| D-Gluconic acid | + |
| N-acetyl-D-Glucosamine | + |
| L-Asparagine | + |
| Glycerol | + |
| D,L-α-Glycerol phosphate | + |
| Glycyl-L-Aspartic acid | + |
| D-Mannose | + |
| D-Glucose-6-Phosphate | + |

The Identification of *Edwardsiella ictaluri* E-ict-VL33 Strain

After a 16S rDNA analysis, the sequence of 16S rDNA of the isolated E-ict-VL33 strain is shown in SEQ ID No: 1. The result of the 16S rDNA analysis and the sequence alignment of the National Center for Biotechnology Information (NCBI) data bank was higher than 99% identified as *E. ictaluri*. This demonstrates that the isolated E-ict-VL33 strain is a member of *E. ictaluri*.

Because some *E. ictaluri* strains have a PEI1 plasmid, the inventor used the ORF1 (open reading frame 1) of the PEI1 plasmid (GenBank accession no: AF244083.1) of an *E. ictaluri* strain as a template to design PCR primers. Sequence of the PEI1 plasmid of the isolated E-ict-VL33 strain was determined by PCR using said primers. After sequencing, a partial sequence of the PEI1 plasmid of the isolated E-ict-VL33 strain is shown in SEQ ID No: 2 (the length of SEQ ID No: 2 is 1876 bp). In a sequence alignment comparing the sequence of SEQ ID NO: 2 with the NCBI data bank, the result indicates that the fragment of the $1^{st}$ nucleotide (nt) to the $1443^{rd}$ nt of SEQ ID NO: 2 is similar with the sequence of the PEI1 plasmid (GenBank accession no: AF244083.1) with 99% identity. However, the fragment of the $1444^{th}$ nt to the $1876^{th}$ nt of SEQ ID NO: 2 is different from the sequence of the PEI1 plasmid (GenBank accession no: AF244083.1). This indicates that the isolated E-ict-VL33 strain is different from the *E. ictaluri* strain with the PEI1 plasmid (GenBank accession no: AF244083.1). Although the isolated E-ict-VL33 strain and the *E. ictaluri* strain with the PEI1 plasmid (GenBank accession no: AF244083.1) are both *E. ictaluri*, they are different strains according to the sequencing result. Therefore, the isolated E-ict-VL33 strain is a novel *E. ictaluri* isolated strain.

The result shows that the isolated *Edwardsiella ictaluri* E-ict-VL33 strain is identified as a novel *Edwardsiella ictaluri* strain, and the E-ict-VL33 strain has been deposited in the ATCC on Mar. 8, 2010, with an ATCC deposit number PTA-10711.

EXAMPLE 2

Preparation of Vaccines

Step 1 Cultivation and Collection of the Bacteria

The bacteria (*Edwardsiella ictaluri* E-ict-VL33 strain) were cultured in Brain Heart Infusion (BHI) broth at 28° C. for 48 hours, then collected in a bacteria suspension.

Step 2 Inactivated Processes

Inactivation of bacteria was done by adding 37% formaldehyde at a final concentration of 0.5% (w/v) to the bacteria suspension obtained in Example 1, and incubating (shaking) the bacteria suspension with formaldehyde at 25° C., 70 rpm for a minimum of 24 hours (preferably 48 hours). The bacteria (*Edwardsiella ictaluri* E-ict-VL33 strain) have to be verified as being completely inactive by a test. The supernatant of the bacteria suspension containing the formaldehyde was separated by using centrifugation at 9000×g to remove the formaldehyde, then suspending the pellet in a buffer solution (such as distilled water, phosphate buffered saline (PBS)). Finally, the vaccine stock containing inactivated antigen can be obtained. The vaccine stock were stored at +4° C.

EXAMPLE 3

Preparation of Immersion Vaccine of *Edwardsiella ictaluri* E-ict-VL33

Vaccine stock obtained in example 2 were prepared as immersion vaccine by suspending the vaccine stock in a buffer solution (such as sterile water or PBS). The content of formaldehyde in the immersion vaccine is lower than 0.2% (v/v).

EXAMPLE 4

Preparation of Oral Vaccine of *Edwardsiella ictaluri* E-ict-VL33

Vaccine stock obtained in example 2 were prepared as a 400 liter oral vaccine by mixing 300 liters of vaccine stock (at least comprising $1.65\times10^{15}$ cfu bacteria), 4 liters of surfactant (polysorbate 80), and 96 liters of fish oil. The antigen of *E. ictaluri* was coated with a two phase oleaginous adjuvant in a w/o/w form by homogenously emulsifying the mixture with a homogenizer with high shear force (10,000 rpm). The oral vaccine can then be obtained. The 400 liter oral vaccine is composed of 24% (v/v) fish oil, 1% (v/v) surfactant, and $3.85\times10^{8}$ cfu/ml inactivated bacteria. The content of formaldehyde in the oral vaccine is lower than 0.2% (v/v).

Use of the Oral Vaccine

The invention also provides the application of the oral vaccine obtained in example 4. The oral vaccine can further be spray coated on the outside of commercially available pelleted feed at 2% (volume/weight). Also, the coated pellet can further be sprayed with squid oil at 0.1% (v/w). The feed can be AQUAXCEL 7434 pelleted feed or other commercially available feed.

EXAMPLE 5

Efficiency of the *Edwardsiella ictaluri* E-ict-VL33 Inactivated Vaccine 5-1. Efficiency Experiment Healthy, non-infected, catfish (*P. hypophthalmus*), locally referred to as Tra fish, were vaccinated using immersion or oral vaccination or combinations of these vaccinations. The various vaccinations or vaccination combinations and challenge preparation were divided into various experiments for the (sub) groups. The various vaccinations or vaccination combinations and challenges were performed in at least 3 different experiments.

Experiment 1: Set up the Challenge Model

A total of about 1500 fish were used to set up the challenge model to be used in the trial.

Bath challenge: Fifty fish per tank in three parallel tanks per dose (with 4 doses total) were challenged by pouring bacteria grown in BHI broth into water to give a final concentration of $5.5\times10^{3}$ to $5.5\times10^{6}$ colony forming units ($5.5\times10^{3}$, $5.5\times10^{4}$, $5.5\times10^{5}$ and $5.5\times10^{6}$) of *E. ictaluri* E-ict-VL33 strain per ml of water. Exposure to the challenge dose lasted for 30 min. Strong aeration was supplied to the water in the tanks during the challenge. The control groups were immersed in clean aerated water. Mortalities were monitored for 14 days.

Injection challenge: Before injecting, fish were anaesthetized with 0.2% MS222 in the water. Fish were injected intraperitoneally with 0.1 ml of a bacterial dilution at 4 different bacterial concentrations ranging from $5.5\times10^{3}$ to $5.5\times10^{6}$ colony forming units (10-fold steps, $5.5\times10^{3}$, $5.5\times10^{4}$, $5.5\times10^{5}$ and $5.5\times10^{6}$) of *E. ictaluri* per ml or sterile saline water for control. Mortalities were monitored for 14 days.

From both experiments, moribund and freshly dead fish were submitted for bacterial isolation from the liver, spleen and kidney. Surviving fish at the end of monitoring period were checked for bacterial infection.

Experiment 2: Immersion/Oral Immunization Studies

Combined immersion/oral immunization studies are summarized in Table 6. The groups included Group A (immersion-prime) with immunization by immersion only (day 1) and challenge at 48 and 121 days after primary vaccination, Group C (imm-oral boost-1) with combined immersion (day 1) and oral boost by days 8 to 21, and Group F (imm-oral boost-2) boosted a second time through experimental days 101 to 107. Group E (oral-prime) was given primary immunization at days 8 to 21 by the oral route and challenged at 48 and 121 days after primary vaccination. Non-vaccinated control groups were challenged at 48 and 121 days.

TABLE 6 outlines how the immersion and oral vaccination of the various fish was done and which groups were challenged using the method established in Experiment 1.

| Group | Number of replicates | primary vaccination | first boost | second boost | Challenge at day 48 (50 fish per parallel) | Challenge at day 121 (40 fish per parallel) |
|---|---|---|---|---|---|---|
| A | 3 | Immersion-prime | — | — | Yes | — |
| | 1 | Immersion-prime | — | — | — | Yes |
| C | 3 | Immersion-prime | Oral (day 8-21) | — | Yes | — |
| | 1 | Immersion-prime | Oral (day 8-21) | — | — | Yes |
| F | 1 | Immersion-prime | Oral (day 8-21) | Oral (day 101-107) | — | Yes |
| E | 3 | Oral (day 8-21) | — | — | Yes | — |
| | 1 | Oral (day 8-21) | — | — | — | Yes |
| Ct | 3 | Non-vaccinated controls | | | Yes | — |
| | 1 | Non-vaccinated controls | | | — | Yes |

Note:
Ct represents the control group and "—" represents the group without performing the treatment.

The process of immersion vaccination, oral vaccination, and immersion challenge are described as follow:

Immersion vaccination: The immersion vaccine consisted of a sterile water-based, killed bacterial suspension of $5.0\times10^{9}$ bacteria per ml Immersion vaccination was performed by immersing 1200 fish in 2 L of vaccine stock diluted in 18 L ($5.56\times10^{8}$ bacteria per ml final concentration) of clean water for 1 min with strong aeration.

Oral vaccination: The outside of feed pellets was spray coated by the oral vaccine obtained in Example 4 (in a w/o/w form, containing $3.85\times10^{8}$ cfu/ml) at 2% (volume/weight). The coated pellets were then sprayed with squid oil at 0.1% (v/w). The coated feed pellets were prepared daily and used within 1 to 2 days after preparation and fed to satiation. The feed can be WOOSUNGVINA Co. J3, J4 feed or other commercially available feed.

Immersion challenge: The immersion challenge was performed in 96 liter tanks containing 70 liters of clean water. At the first challenge (day 48), 40 or 50 fish (number of fish depending on the experiment) from each tank were transferred to a bucket containing 10 liter of clean water and then bacteria grown in BHI broth was poured into the water to given concentrations of $7.6\times10^{6}$ or $4.3\times10^{6}$ bacteria/ml of water for Experiments 2 and 3, respectively. Exposure to the challenge dose lasted for 1 h. At the second challenge (121 days), the same immersion method was applied with a concentration of $8.1\times10^6$ bacteria/ml of water for Experiments 2. The non-challenged controls were immersed in clean aerated water. After challenge the fish were observed for 14 days.

Statistical Analysis

Fisher's exact test was used to analyze differences between groups at end-point. A P-value below 0.05 was considered to represent significant differences between groups/treatments.

5-2. Results

Experiment 1

In this experiment, challenge by immersion was compared with challenge by injection. For immersion challenge the end-point mortality varied from 1.3% (±1.15 SD) at $5.5\times10^3$ cfu/ml to 66% (±8.5 SD) at $5.5\times10^6$ cfu/ml. For the injection challenge, it ranged from 93 (±1.5 SD) to 99.3% (±0.6 SD) end-point mortality over the dose range tested. Based on these results, immersion challenge was used for assessing vaccination efficacy and it was considered that the immersion dose of $>10^6$ gave sufficient mortality, i.e. more than 60% control mortality.

Experiment 2

Figure 2:
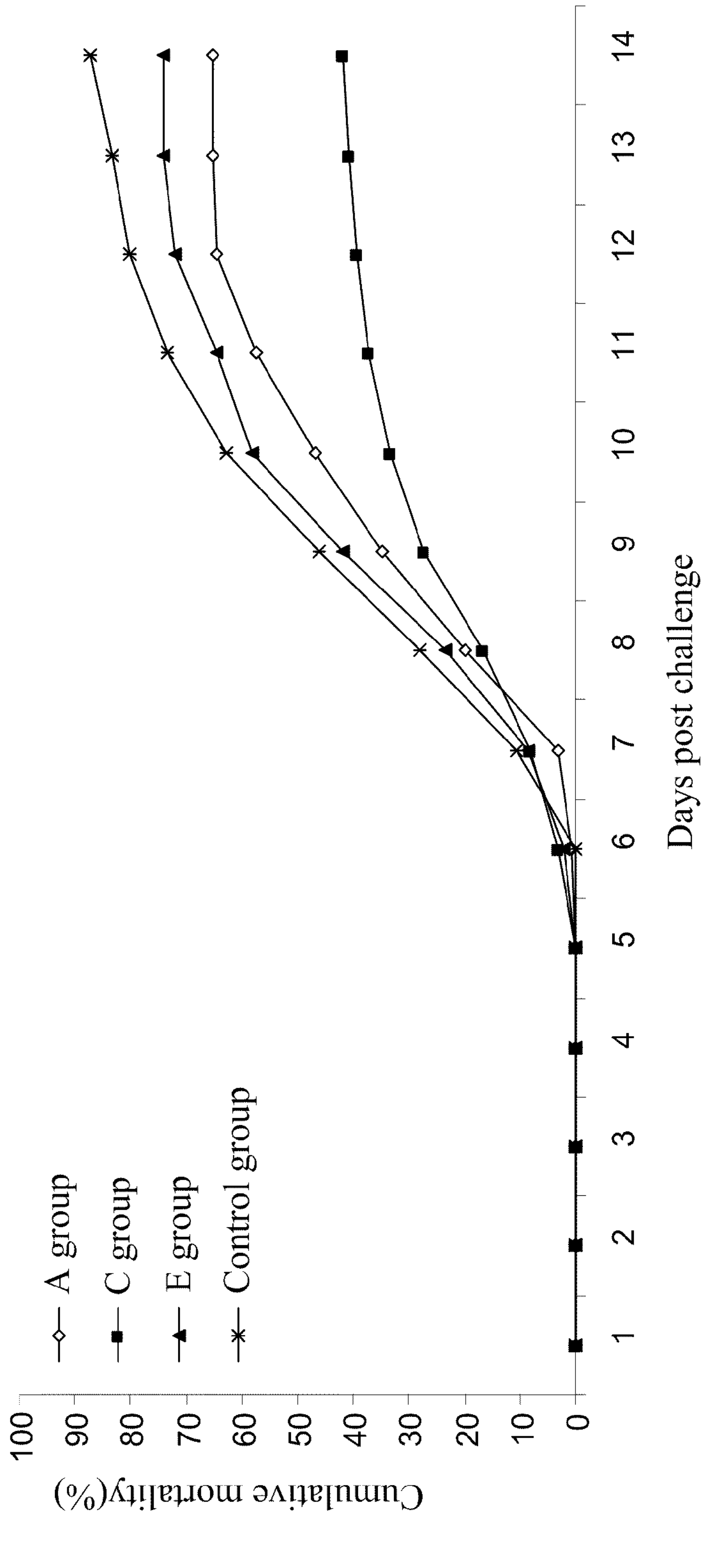
FIG. 2 shows the cumulative mortality (%) obtained after challenge performed at 48 days post-vaccination using an immersion challenge in Groups A, C and E.

Referring to FIG. 2 and Table 7, immersion/oral immunization studies (Experiment 2) showed a cumulative mortality in the non-vaccinated controls of 87% by day 48. In Group A (immersion-prime) the average cumulative mortality was 65% (±3.1 S.D.) ($p<0.02$), while in Group E (oral prime) average, cumulative mortality was 74%±3.5 ($p>0.1$), and in Group C (imm-oral boost-1) average cumulative mortality was 42%±4.0, ($p<0.001$), giving RPS values of 25, 15, and 52, respectively. The results indicate clearly that the fish given a combination of immersion and oral boost (C group) were much better protected than the fish in the other groups (A or E group).

Relative Percent Survival (RPS)=(1−(% mortality in vaccinated fish/% mortality in control))×100.

TABLE 7

Cumulated mortality of the vaccinated and control fish in experiment 2 at first challenge (experiment day 48; 27 days post completion of oral boost).

| Days after challenge | Vaccination method/group: Immersion (only) A1 | A2 | A3 | Immersion/oral (1×) C1 | C2 | C3 | Oral (only) E1 | E2 | E3 | Control Ct1 | Ct2 | Ct3 |
|---|---|---|---|---|---|---|---|---|---|---|---|---|
| 1 | 0 | 0 | 0 | 0 | 0 | 0 | 0 | 0 | 0 | 0 | 0 | 0 |
| 2 | 0 | 0 | 0 | 0 | 0 | 0 | 0 | 0 | 0 | 0 | 0 | 0 |
| 3 | 0 | 0 | 0 | 0 | 0 | 0 | 0 | 0 | 0 | 0 | 0 | 0 |
| 4 | 0 | 0 | 0 | 0 | 0 | 0 | 0 | 0 | 0 | 0 | 0 | 0 |
| 5 | 0 | 0 | 0 | 0 | 0 | 0 | 0 | 0 | 0 | 0 | 0 | 0 |
| 6 | 1 | 0 | 0 | 0 | 0 | 1 | 1 | 2 | 0 | 0 | 0 | 0 |
| 7 | 4 | 0 | 3 | 2 | 1 | 4 | 3 | 3 | 4 | 7 | 6 | 3 |
| 8 | 9 | 6 | 7 | 4 | 3 | 4 | 6 | 10 | 6 | 10 | 10 | 6 |
| 9 | 11 | 7 | 4 | 6 | 5 | 6 | 10 | 7 | 11 | 6 | 12 | 9 |
| 10 | 5 | 8 | 5 | 5 | 4 | 5 | 8 | 4 | 12 | 7 | 6 | 12 |
| 11 | 3 | 4 | 9 | 1 | 3 | 2 | 5 | 4 | 1 | 7 | 4 | 5 |
| 12 | 1 | 5 | 5 | 1 | 1 | 0 | 2 | 5 | 4 | 1 | 2 | 7 |
| 13 | 0 | 1 | 0 | 2 | 1 | 1 | 3 | 0 | 0 | 3 | 2 | 0 |
| 14 | 0 | 0 | 0 | 0 | 1 | 0 | 0 | 0 | 0 | 2 | 2 | 2 |
| Total mortality | 34 | 31 | 33 | 21 | 19 | 23 | 38 | 35 | 38 | 43 | 44 | 44 |
| No. of fish/tank | 50 | 50 | 50 | 50 | 50 | 50 | 50 | 50 | 50 | 50 | 50 | 50 |
| Mortality (%) | 68 | 62 | 66 | 42 | 38 | 46 | 76 | 70 | 76 | 86 | 88 | 88 |
| Average mortality | | 65% | | | 42% | | | 74% | | | 87% | |
| RPS | | 25 | | | 52 | | | 15 | | | — | |

Figure 3:
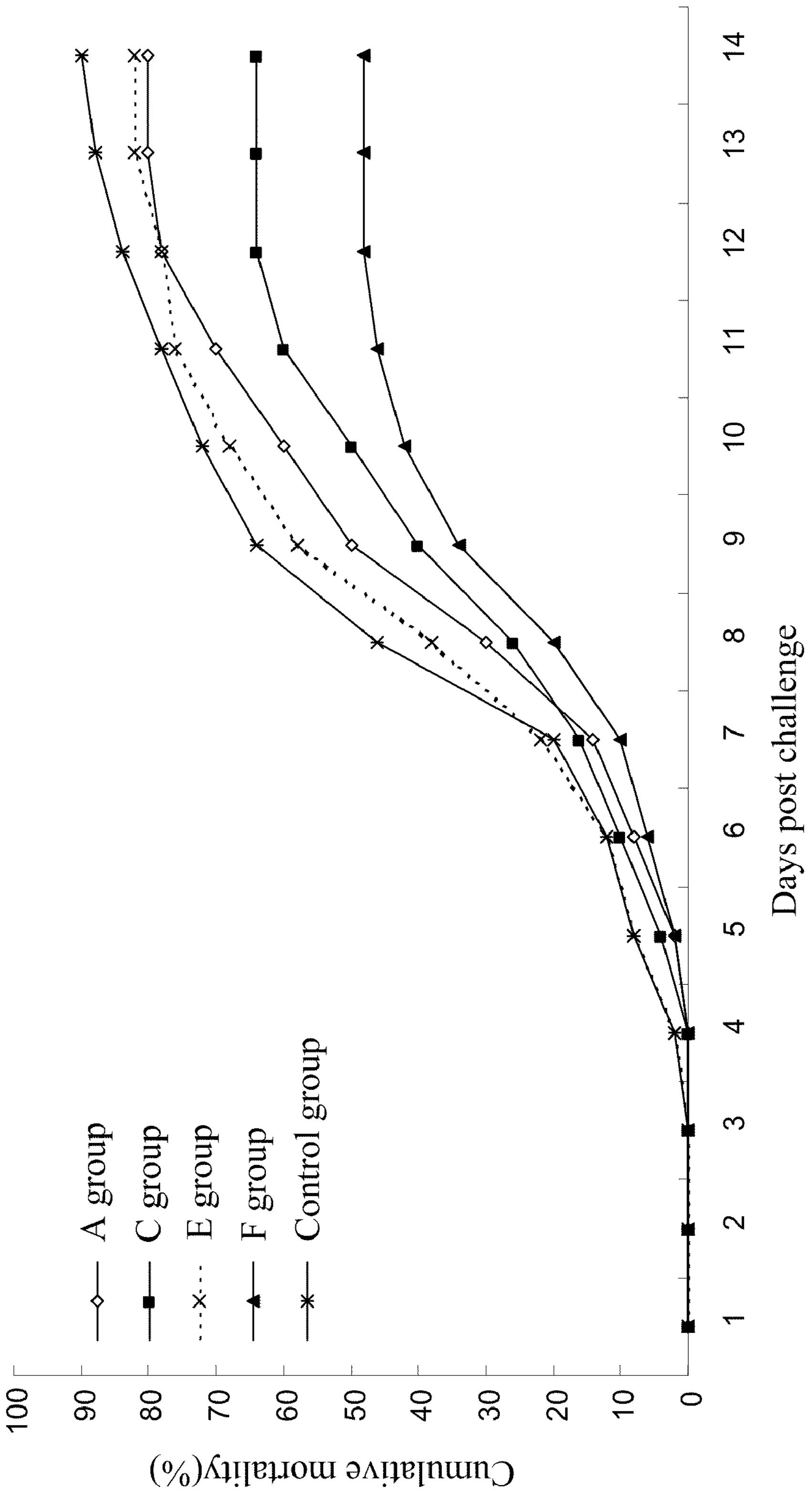
FIG. 3 shows the cumulative mortality (%) obtained after immersion challenge at 121 days post-primary immunization for Groups A, C, E and F.

Referring to FIG. 3 and Table 8, the second challenge was performed at Experimental day 121 and fish were given a challenge dose of $8.1\times10^6$ cfu/ml of water. Cumulated mortality in the different vaccine groups and the control fish is shown in Table 10. At experimental day 121 the cumulative mortality in the controls was 90%. In Group A (immersion-prime) cumulative mortality was 80% (RPS=11, p=0.26), while Group E (oral prime) showed a mortality of 82% (RPS=9, p=0.388). In Group C (imm-oral boost-1) mortality was 64% (RPS=29, p=0.0037) while in Group F (imm-oral boost-2) cumulative mortality was 48% (RPS=47, p=0.0001). From the statistical evaluation only a combined vaccination of immersion/oral gives significant protection over the controls and single immunization procedures.

TABLE 8

Cumulated mortality of the vaccinated and control fish in experiment 2 at second challenge (experiment day 121).

| Days after challenge | Vaccination regimes/Group: Immersion A | Immersion/oral (21d) C | Oral E | Controls Ct | Immersion/oral (2 boost; 21 day and 107*) F |
|---|---|---|---|---|---|
| 1 | 0 | 0 | 0 | 0 | 0 |
| 2 | 0 | 0 | 0 | 0 | 0 |
| 3 | 0 | 0 | 0 | 0 | 0 |
| 4 | 0 | 0 | 1 | 1 | 0 |
| 5 | 1 | 2 | 3 | 3 | 1 |
| 6 | 3 | 3 | 2 | 1 | 2 |
| 7 | 3 | 3 | 5 | 4 | 2 |
| 8 | 8 | 5 | 8 | 13 | 5 |
| 9 | 10 | 7 | 10 | 9 | 7 |
| 10 | 5 | 5 | 5 | 4 | 4 |
| 11 | 5 | 5 | 4 | 3 | 2 |
| 12 | 4 | 2 | 1 | 3 | 1 |
| 13 | 1 | 0 | 2 | 2 | 0 |
| 14 | 0 | 0 | 0 | 2 | 0 |
| Total mortality | 40 | 32 | 41 | 45 | 24 |
| Total number of fish/tank | 50 | 50 | 50 | 50 | 50 |
| Mortality (%) | 80 | 64 | 82 | 90 | 48 |
| RPS | 11 | 29 | 9 | — | 47% |

*the numbers indicate the experiment days that the oral boost feeding ended

The results show that a single immersion or oral immunization regime confers low protective immunity at long term post immunization. A combination of immersion and one oral boost is superior to the immersion (only) method. A second boost initiated 80 days after the first boost and completed 21 days before challenge resulted in an increased level of protection and gives a RPS=47 at a control mortality of 90%.

Together these findings show that a primary immunization with combined immersion and oral delivery induces a strong and long-lasting immunity Immunized fish benefit significantly from a second boost via the oral route.

In summary, the invention provides:

1. A novel *Edwardsiella ictaluri* E-ict-VL33 strain.

2. Vaccines derived from the novel *Edwardsiella ictaluri* E-ict-VL33 strain.

3. A method for improving the immunity of fishes against *Edwardsiella ictaluri*, further preventing and promoting fishes from the infection of *Edwardsiella ictaluri.*

Many changes and modifications in the above described embodiment of the invention can, of course, be carried out without departing from the scopes thereof. Accordingly, to promote the progress in science and the useful arts, the invention is disclosed and is intended to be limited only by the scope of the appended claims.

What is claimed is:

1. A novel purified and isolated *Edwardsiella ictaluri* E-ict-VL33 strain which is ATCC deposit number PTA-10711.

2. A vaccine composition comprising the *Edwardsiella ictaluri* E-ict-VL33 strain as recited in claim 1, which is prepared from the inactivation of *Edwardsiella ictaluri* E-ict-VL33 strain by an inactivation agent.

3. The vaccine composition as recited in claim 2, wherein said inactivation agent is formaldehyde or binary ethylene-imine (BEI).

4. The vaccine composition as recited in claim 2, further comprising a pharmaceutically acceptable vehicle.

5. The vaccine composition as recited in claim 4, wherein the pharmaceutically acceptable vehicle is selected from the group consisting of at least one of solvent, emulsifier, suspending agent, decomposer, binding agent, excipient, stabilizing agent, chelating agent, diluent, gelling agent, preservative, lubricant, surfactant, and adjuvant.

6. The vaccine composition as recited in claim 5, wherein the pharmaceutically acceptable vehicle is an adjuvant is selected from the group consisting of at least one of oleaginous adjuvant, aqueous adjuvant, two-phase oleaginous adjuvant, and biological adjuvant.

7. The vaccine composition as recited in claim 6, wherein the adjuvant is an oleaginous adjuvant, selected from the group consisting of at least one of mineral oil, plant oil, animal oil, Freund's Complete Adjuvant and Freund's Incomplete Adjuvant.

8. The vaccine composition as recited in claim 6, wherein the adjuvant is an aqueous adjuvant, wherein the aqueous adjuvant is aluminium hydroxide.

9. The vaccine composition as recited in claim 6, wherein the adjuvant is two-phase oleaginous adjuvant wherein the two-phase oleaginous adjuvant comprises a surfactant and an oleaginous substance.

10. The vaccine composition as recited in claim 9, wherein the surfactant is selected from the group consisting of: at least one of sorbitol fatty acid ester, the concentrate of sorbitol fatty acid ester and ethylene oxide or propylene oxide, mannitol fatty acid ester, the concentrate of mannitol fatty acid ester and ethylene oxide or propylene oxide, modified mannitol fatty acid ester with a hydrophilic group which is selected from the group consisting of: at least one of carboxylic acid, amine, amide, alcohol, polyol, ether and oxide; anhydromannitol fatty acid ester, modified anhydromannitol fatty acid ester with a hydrophilic group which is selected from the group consisting of: at least one of carboxylic acid, amine, amide, alcohol, polyol, ether and oxide; saccharose fatty acid ester, the concentrate of saccharose fatty acid ester and ethylene oxide or propylene oxide, glycerol fatty acid ester, the concentrate of glycerol fatty acid ester and ethylene oxide or propylene oxide, the concentrate of fatty acid and ethylene oxide or propylene oxide, the concentrate of fatty alcohol and ethylene oxide or propylene oxide, and glycerophospholipid.

11. The vaccine composition as recited in claim 9, wherein the oleaginous substance is selected from the group consisting of: at least one of mineral oil, plant oil and animal oil.

12. The vaccine composition as recited in claim 6, wherein the adjuvant is biological adjuvant wherein the biological adjuvant is selected from the group consisting of at least one of oligonucleotide and toxoid.

* * * * *